United States Patent [19]

Weeks

[11] Patent Number: Plant 5,452

[45] Date of Patent: Apr. 30, 1985

[54] ROSE PLANT

[76] Inventor: O. L. Weeks, 926 W. Philadelphia, Ontario, Calif. 91761

[21] Appl. No.: 540,411

[22] Filed: Oct. 11, 1983

[51] Int. Cl.[3] ..... A01H 5/00

[52] U.S. Cl. ..... Plt./18

[58] Field of Search ..... Plt./18

*Primary Examiner*—Robert E. Bagwill

*Attorney, Agent, or Firm*—Vincent G. Gioia

[57] ABSTRACT

A new Neyron rose colored hybrid tea rose variety.

1 Drawing Figure

The present invention relates to a new and distinct variety of rose plant of the hybrid tea rose class, which was originated by my crossing as seed parent the rose known as "Song of Paris" (U.S. Plant Pat. No. 2,669) and the rose known as "Royal Highness" (U.S. Plant Pat. No. 2,032) as pollen parent. The denomination of this new rose is "Lady".

Among the novel characteristics possessed by this new variety which distinguish it from its parents and all other varieties of which I am aware are its attractive Neyron rose flowers borne almost singly, one to a stem, produced prolifically on an outstanding plant. Flowers are of good exhibition form and are desirable for cutting as well as garden decoration. The foliage is particularly outstanding which with the fine plant growth habit and beautiful flowers result in a most satisfactory new cultivar. Asexual reproduction by budding of the new variety as performed in Kern County, Calif., shows that the foregoing and other distinguishing characteristics come true to form and are established and transmitted through succeeding propagations.

The new variety has none of the lavender shadings of its seed parent "Song of Paris" and has a far superior plant and foliage. Flower form is different than pollen parent "Royal Highness" and plant is larger growing and more robust.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The terminology used in color description herein refers to plate numbers in the aforementioned color chart, e.g., "55B" is plate 55B of The Royal Horticultural Society Colour Chart.

Parentage: Seedling.

*Seed parent.*—"Song of Paris".

*Pollen parent.*—"Royal Highness".

Class: Hybrid Tea.

The following observations are made of specimens grown outdoors in Kern County, Calif., during the month of August.

FLOWER

Blooming habit: Recurrent.

Bud:

(1) *Size.*—Medium.

(2) *Form.*—Long pointed.

(3) *Color.*—After sepals divide, buds are light Neyron rose blending to petal edge to deeper tonality near 55B.

(4) *Sepals.*—Slightly longer than bud, two with straight edges, two with fringed edges.

(5) *Peduncle.*—Length — long. Aspect — upright, small prickles. Strength — erect. Color — yellowish green.

Bloom:

(1) *Size.*—Average size when fully expanded — about $4\frac{1}{2}$ inches.

(2) *Borne.*—Singly, one to a stem.

(3) *Form.*—High centered, petals roll downward, moderately ruffled at maturity.

(4) *Petalage.*—Number of petals under normal conditions — about 35 to 40.

(5) *Color.*—After sepals fall and petals unfurl, outer petals appear to lighten in tonality in contrast to inner petals still bunched. Color range is 55D (outer petals) to Neyron rose 55B (flower center). Petal top and bottom surfaces appear of similar hue. As flower matures to full open stage Neyron rose coloring, near 55C. to D, appears more uniform. Individual petals are moderately ruffled and occasionally have deeper Neyron rose edges.

Petals:

(1) *Texture.*—Thick and heavy.

(2) *Appearance.*—Inside and outside velvety.

(3) *Form.*—Acuminate.

(4) *Arrangement.*—Imbricated.

(5) *Petaloids in center.*—Few, large.

(6) *Persistence.*—Drop off cleanly.

(7) *Fragrance.*—Slight.

(8) *Lasting quality.*—Long lasting quality on plant and 3 to 4 days as cut flower.

REPRODUCTIVE ORGANS

Stamens, filaments and anthers:

*Arrangement and color.*—Reddish yellow stamens irregularly arranged around styles.

Pollen:

*Color.*—Yellow.

Styles: Uneven, short, spread out in center.

Stigmas:

*Color.*—Yellow.

Hips: None observed.

PLANT

Form: Upright, compact.

Growth: Vigorous, uniform branched.

*Height attained.*—About 5 feet.

Foliage: Compound 5 leaflets, many 3 leaflets.

(1) *Size.*—Large.

(2) *Quantity.*—Abundant.

(3) *Color.*—New foliage: Upper side — near to 144A, bronze edge. Under side — near to 144A with bronze overlay. Old foliage: Upper side — near 138A. Under side — near to 146B to C.

(4) *Shape.*—Oval.

(5) *Texture.*—Upper side is waxy and veined and under side is dull and veined.

(6) *Edge.*—Serrate.

(7) *Serration.*—Small, light.

(8) *Leaf stem.*—Color — near to 138B. Under side — near 138B.

(9) *Stipules.*—Slightly bearded, long, curving outward.

(10) *Resistance to disease.*—Mildew — average.

Wood:

(1) *New wood.*—Color — near 138A to B. Bark — smooth, waxy.

(2) *Old wood.*—Color — near 138A. Bark — smooth.

Thorns:

(1) *Thorns.*—Quantity (main stalk) — few. On laterals from stalk — few. Form — narrow, pointing downward. Length — medium. Color — reddish light green. Position — regular.

(2) *Prickles.*—Few to none.

Winter hardiness: Needs winter protection in severe climate.

I claim:

A new and distinct variety of rose plant of the hybrid tea rose class, substantially as shown and described, characterized particularly by Neyron rose colored flowers of good exhibition form borne one to a stem on an attractive, vigorous plant.

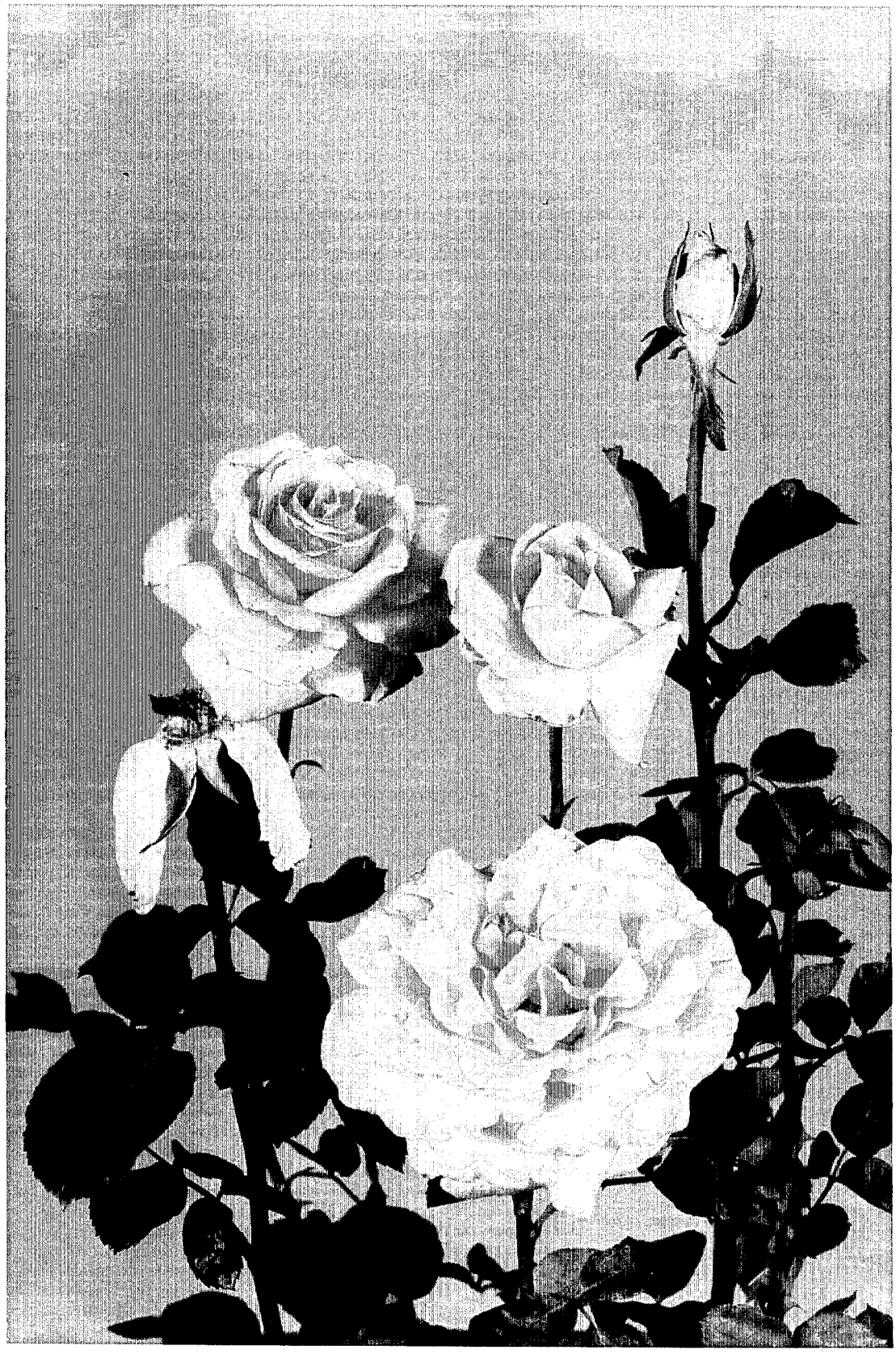

* * * * *